US00PP09127P

United States Patent [19]

Gibeault et al.

[11] Patent Number: Plant 9,127

[45] Date of Patent: May 2, 1995

[54] ZOYSIAGRASS PLANT NAMED 'DE ANZA'

[75] Inventors: Victor A. Gibeault, Riverside; Matthew K. Leonard, Romoland; Victor B. Youngner, deceased, late of Riverside; Violet E. Janowitz, heir, Corona, all of Calif.

[73] Assignee: The Regents of the University of California, Alameda, Calif.

[21] Appl. No.: 181,860

[22] Filed: Jan. 13, 1994

[51] Int. Cl.[6] ..... A01H 5/00

[52] U.S. Cl. ..... Plt./90

[58] Field of Search ..... Plt. 90

*Primary Examiner*—James R. Feyrer

*Attorney, Agent, or Firm*—Christie, Parker & Hale

[57] ABSTRACT

A new and distinct variety of Zoysiagrass which has a longer growing season and green color retention in winter and less anthocyanin than the variety 'El Toro'.

3 Drawing Sheets

BACKGROUND OF THE INVENTION

The present invention relates to a new and distinct variety of Zoysia sp., which is a member of the Gramineae family. The parents of 'De Anza', also referred to herein as 'Z88-8' are native to Asia.

The new variety is the result of crossing the Zoysiagrass variety 'El Toro' (U.S. Plant Pat. No. 5,845) as the female parent and an unnamed proprietary seedling indentified as UC #3 as the male parent. Hand pollination was performed under greenhouse conditions and seed was germinated under laboratory conditions. Seedlings were individually cultured in a greenhouse before transplanting into a field for evaluation and selection. The varietal denomination of the new variety is 'Z88-8' and the commercial name is 'De Anza'. The new variety is a sibling of the variety 'Victoria' which is the subject of plant patent application Ser. No. 08/180,899, filed Jan. 13, 1994.

Sustained drought conditions in California have additionally increased the need for improved warm season turf grass varieties. Zoysiagrasses are well adapted for use under such conditions because of their low water use rates and high tolerance, however, acceptance has been low primarily due to loss of green coloration during the winter months as such grasses routinely go into dormancy.

'El Toro' Zoysiagrass is a much faster-growing variety of Zoysiagrass than others of the species, and it made Zoysiagrass more attractive to commercial sod producers. However, although 'El Toro' exhibits a longer growing season than previously available commercial Zoysiagrass varieties, it does not remain green all year and also tends to turn purple during the onset of winter dormancy. In addition, the leaf texture of 'El Toro' is considered to be somewhat coarse. The new variety is an improvement over Zoysiagrass germplasm available for use as turf grass such as 'El Toro' Zoysiagrass.

SUMMARY OF THE INVENTION

The new variety of Zoysiagrass, 'De Anza', exhibits an extended growing season and longer retention of green coloration during the winter season than presently available commercial Zoysiagrass varieties, including 'El Toro'. Under moderate climatic conditions such as coastal areas of California, acceptable green color quality can be maintained throughout the year. The new variety is vegetatively propagated from sod, plugs, tillers or stolon and rhizome pieces. Asexual propagation by rhizomes and tillers in Riverside County, Calif. has established that the combination of characteristics of the new variety are transmitted through succeeding propagations. Seed viability has not been determined.

Comparison to 'El Toro'

'De Anza' differs from the Zoysiagrass variety 'El Toro' in the length of the growing season and in retention of green color during winter. The new variety also has narrower leaves and produces a finer-textured turf than 'El Toro' and does not produce purple leaf pigmentation upon entering dormancy, as is typical of 'El Toro' Zoysiagrass.

BRIEF DESCRIPTION OF THE ILLUSTRATIONS

The accompanying illustrations show typical specimens of the vegetative growth of the new variety depicted in color as nearly true as it is reasonably possible to make the same in color illustrations of this character.

DESCRIPTION OF THE NEW VARIETY

Because of its heritage, the new variety 'De Anza' is a hybrid of three Zoysiagrass species, *Z. japonica, Z. matrella* and *Z. tenuifolia*. It forms a moderately dense turf that spreads by way of tillers, stolons and rhizomes.

Leaf blades of the new variety are flat and bright green in coloration, near R.H.S. 138A to B, and range from about 1.8 to about 7.2 cm in length, with an average length of about 4.4 cm. The leaf width ranges from about 1.9 to about 3.3 mm with an average leaf width of about 2.6 mm. The shorter leaves are lanceolate in shape while longer leaves become linear. Leaves are rolled in the bud and the ligule is a fringe of hairs. Auricles are absent.

Stolons of 'De Anza' are green to reddish purple in color and stolon internode length ranges from about 1.6 to about 4.5 cm with an average internode length of about 2.7 cm. The stem thickness of internodes ranges from about 1.1 to about 1.5 mm with an average thickness of about 1.3 mm.

In its inflorescence, 'De Anza' exhibits a spike-like raceme ranging from about 1.3 to about 2.3 cm in length with an average of about 1.8 cm. Spikelets average about 2.9 mm in length with a range of about 2.2 to 3.4 mm. The peduncles are green and the spikelets are light green to purplish red, becoming straw-colored when mature.

The new variety, like other Zoysiagrasses, is vegetatively propagable from sod, plugs or stolon or rhizome pieces. It performs best in full sun and is best adapted to warmer climates where heat and drought stress occur. Near-freezing night temperatures will reduce color quality, and prolonged exposure to freezing or near freezing temperatures will induce dormancy. The turf formed by the new cultivar is suitable for situations requiring a durable, high quality lawn that is tolerant of heat and drought stress and is resistant to pests. Such applications would include home lawns, parks and other public planting areas and golf courses.

Figure 1:
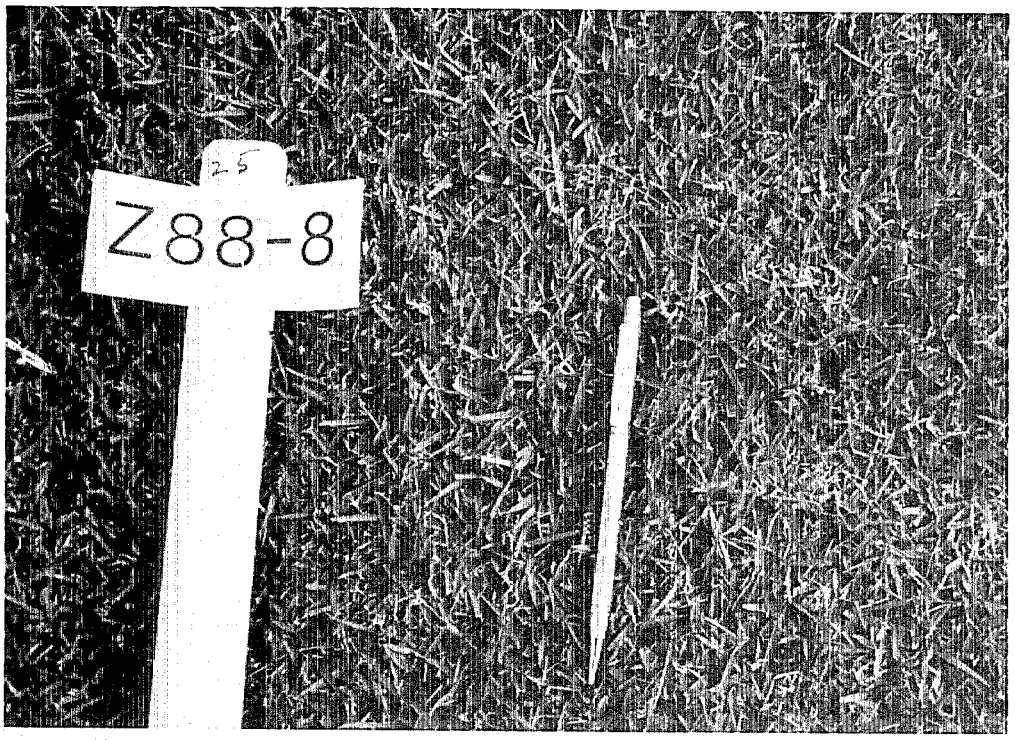
FIG. 1 shows the turf appearance of the new variety on Oct. 15, 1993.
Figure 2:
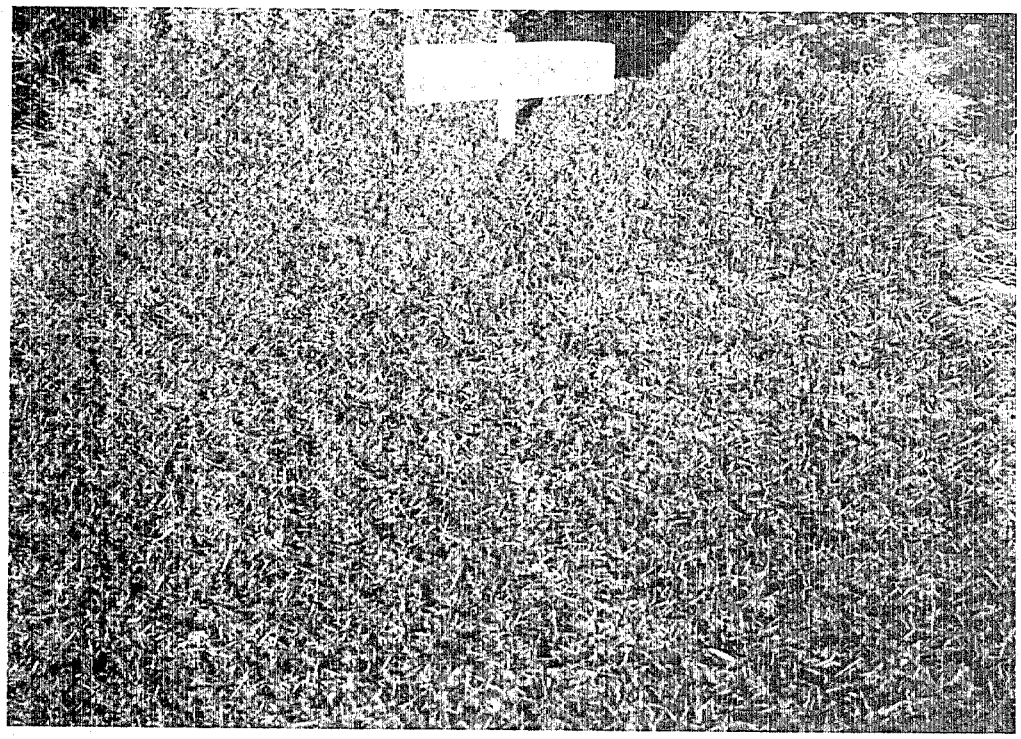
FIG. 2 shows the color of the new variety in December 1991.
Figure 3:
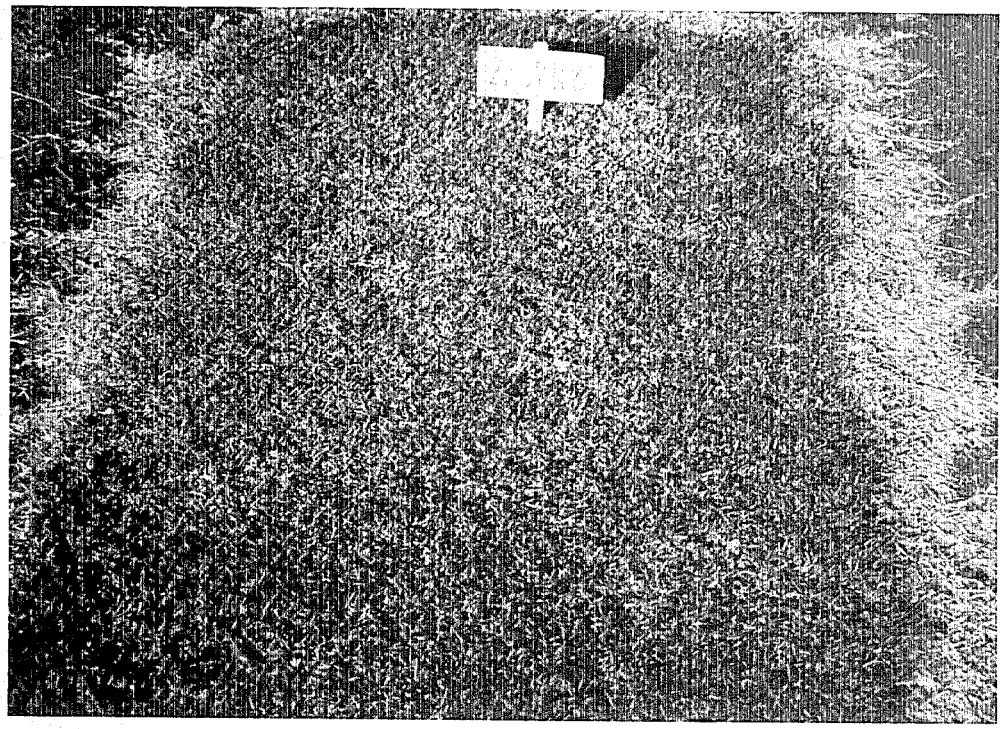
FIG. 3 shows the color of 'El Toro' in December 1991.
Figure 4:
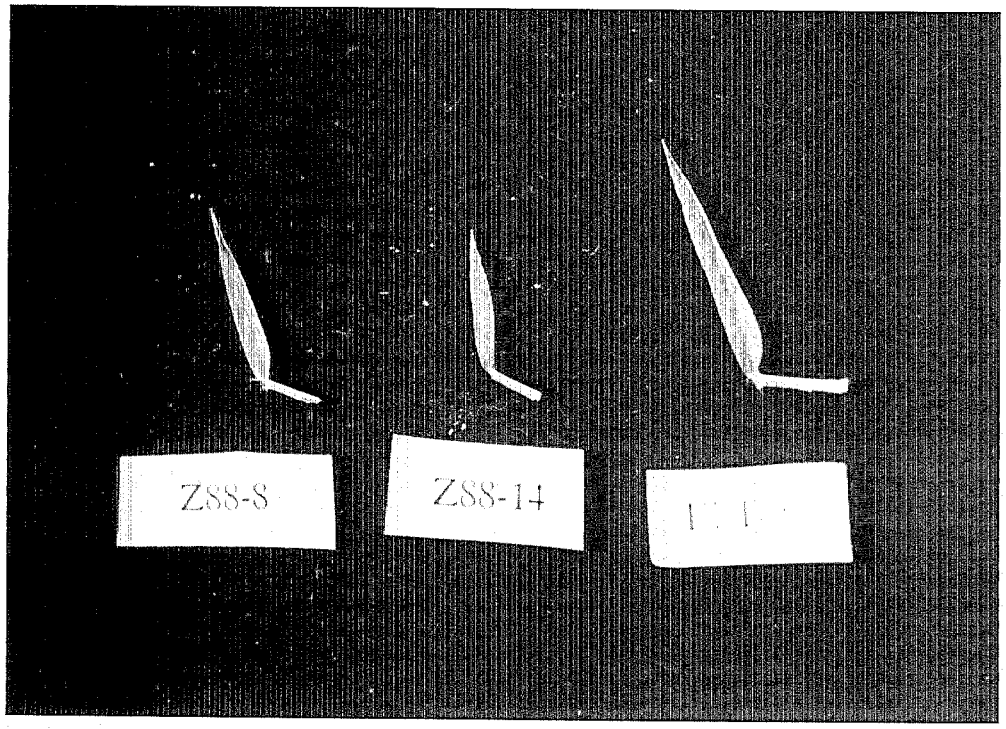
FIG. 4 shows the appearance of a single leaf of the new variety as compared to another new variety which is the subject of co-pending U.S. plant patent application Ser. No. 08/180,899, filed Jan. 3, 1994, and 'El Toro'.
Figure 5:
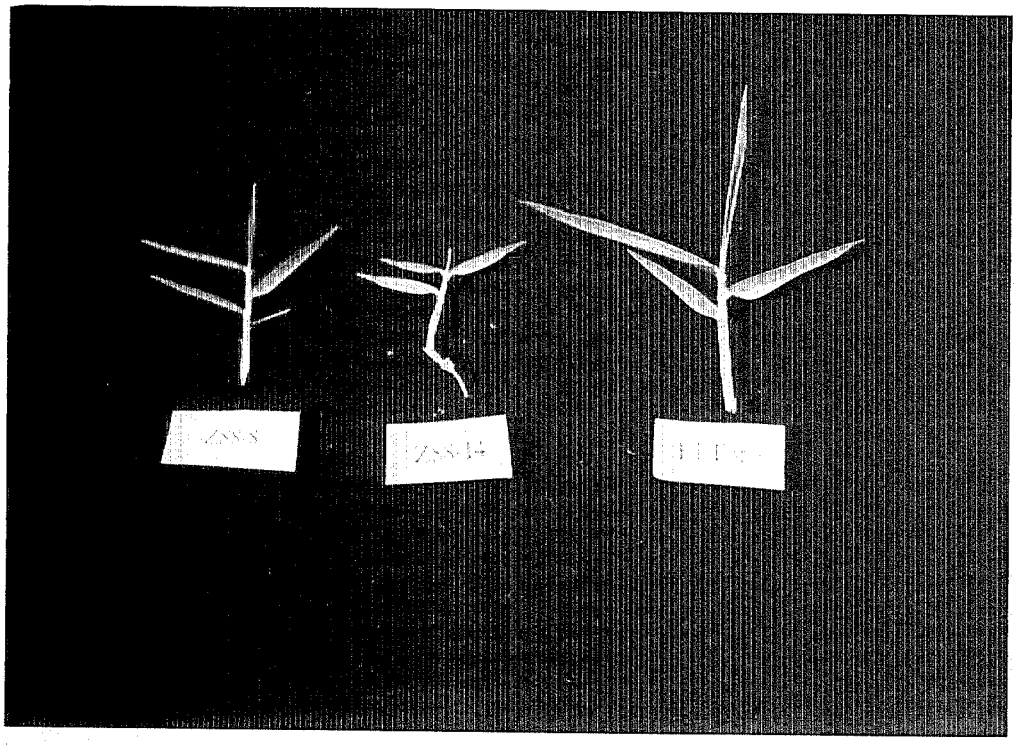
FIG. 5 depicts the leaf orientation of the same three Zoysiagrass lines identified in FIG. 4.
Figure 6:
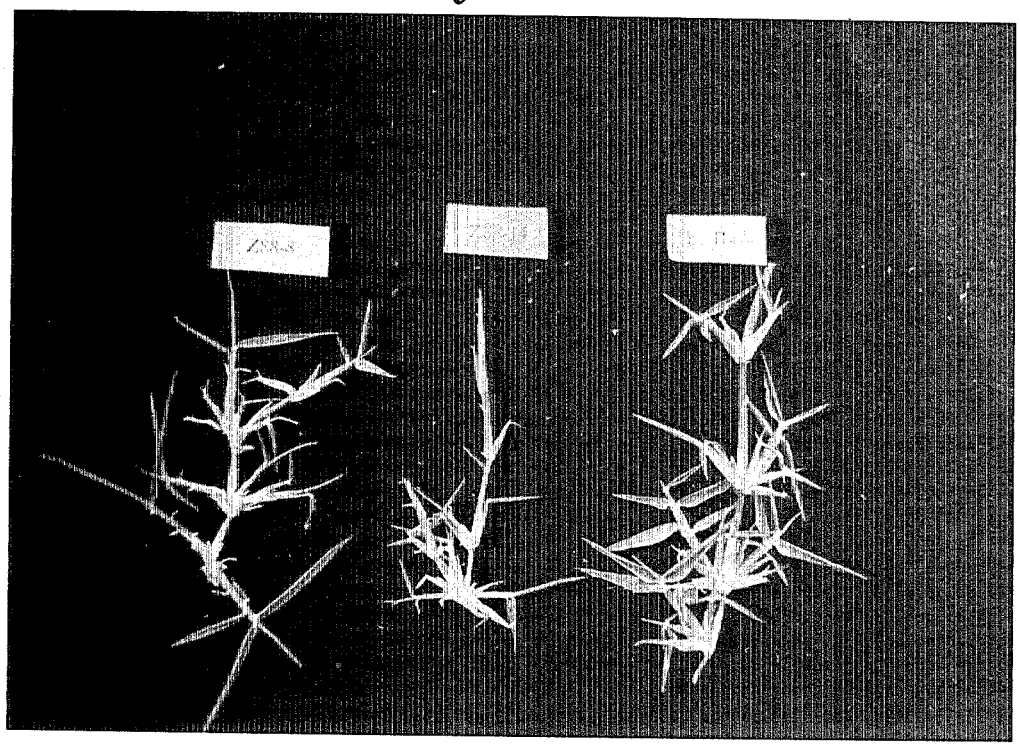
FIG. 6 shows stolons of a new variety also compared with the variety of the aforementioned co-pending application and 'El Toro' to illustrate the difference in purple pigmentation (anthocyanin) as compared to the variety 'El Toro' on Oct. 15, 1993.

The accompanying illustrations serves to illustrate the distinctive features of the new variety. As can be seen from FIGS. 1–6, 'De Anza', identified as 'Z88-8' differs from the other new variety compared with 'Z88-8' and also from 'El Toro'. In particular, the difference in winter color is shown in FIGS. 2 and 3 and the difference in purple pigmentation from 'El Toro' and the new variety is shown in FIG. 5.

To further illustrate the difference between the new variety and 'El Toro', tests were conducted at the University of California at Riverside and the University of California South Coast Field Station (SCFS) at Irvine, Calif., to compare the winter color of Zoysiagrasses. The results of these evaluations are shown in Tables I and II. Statistical differences among the cultivars were determined using the Duncan's Multiple Range Test. Values given in Tables I and II that are followed by the same letters are not significantly different from each other at the 5% level of probability. For these comparisons, plugs of the grasses were placed on one-foot centers with each replicated three times. Common management practices were used during the 1991–92 period, and after establishment, the grasses were mowed at ¾-inch height at UC SCFS, and ⅝ inch at UC Riverside. The grasses were irrigated as needed based on evapotranspiration from an on-site CIMIS station at both locations and were fertilized at about 6 pounds nitrogen per 1000 square feet of turf area. Tables I and II present the fall/winter color of the grasses on a regular basis, at both test sites, from November 1992 through March 1993 using a rating system of 1 to 9 with 1 representing dormant turf and 9 representing full green color. Also shown are the soil temperatures in °F. at 4 inches depth for each observation date. Normal soil temperatures at UC SCFS did not go as low as Riverside. Once the temperatures went below 50° F. (at UC Riverside), 'El Toro' exhibited considerable color loss while the new variety continued to have acceptable green coloration.

TABLE I

| | OBSERVATION DATE | | | | |
|---|---|---|---|---|---|
| GRASS | 10-26-92 | 11-2-92 | 11-10-92 | 11-16-92 | 11-23-92 |
| 'El Toro' | 7.7 bcde | 6.7 cde | 7.0 bcd | 7.0 abcde | 6.3 bcde |
| 'Z88-8' | 9.0 a | 8.0 a | 8.3 a | 8.3 a | 7.7 a |
| 'Z88-14' | 8.7 ab | 7.7 ab | 7.7 abc | 7.3 abcd | 6.7 abcd |
| Avg. soil temp. (°F.) | 68 | 68 | 63 | 62 | 61 |

| | OBSERVATION DATE | | | |
|---|---|---|---|---|
| GRASS | 11-30-92 | 12-14-92 | 12-21-92 | 12-31-92 |
| 'El Toro' | 6.0 abcde | 4.0 defg | 4.0 cd | 3.3 cd |
| 'Z88-8' | 7.7 a | 7.3 a | 6.7 a | 6.3 a |
| 'Z88-14' | 7.7 a | 6.3 abc | 6.0 ab | 5.3 ab |
| Avg. soil temp. (°F.) | 58 | 56 | 53 | 54 |

| | OBSERVATION DATE | | | |
|---|---|---|---|---|
| GRASS | 1-4-93 | 1-20-93 | 1-25-93 | 2-1-93 |
| 'El Toro' | 3.0 def | 3.3 de | 4.0 fg | 4.3 de |
| 'Z88-8' | 6.3 a | 7.0 ab | 7.3 ab | 7.7 ab |
| 'Z88-14' | 5.3 ab | 6.0 b | 6.0 cd | 6.7 bc |
| Avg. soil temp. (°F.) | N/A | 56 | 57 | 56 |

| | OBSERVATION DATE | | | |
|---|---|---|---|---|
| GRASS | 2-8-93 | 2-16-93 | 2-22-93 | 3-1-93 |
| 'El Toro' | 4.3 e | 5.3 efg | 6.0 cde | 5.7 bcd |
| 'Z88-8' | 7.0 ab | 8.0 ab | 8.0 a | 7.7 a |
| 'Z88-14' | 5.7 cd | 6.3 cde | 6.9 abcd | 6.5 abc |
| Avg. soil temp. (°F.) | 57 | 58 | 58 | 55 |

TABLE II

| | OBSERVATION DATE | | | | |
|---|---|---|---|---|---|
| GRASS | 11-4-92 | 11-13-92 | 11-20-92 | 11-26-92 | 12-4-92 |
| 'El Toro' | 9.0 a | 8.7 ab | 8.0 a | 7.3 ab | 6.7 bcde |
| 'Z88-8' | 9.0 a | 9.0 a | 8.0 a | 7.7 ab | 8.0 a |
| 'Z88-14' | 8.7 ab | 8.7 ab | 7.7 ab | 7.7 ab | 7.7 ab |
| Avg. soil temp. (°F.) | 64 | 58 | 58 | 52 | 50 |

| | OBSERVATION DATE | | | |
|---|---|---|---|---|
| GRASS | 12-14-92 | 12-21-92 | 12-31-92 | 1-8-93 |
| 'El Toro' | 4.7 def | 3.0 ef | 1.7 ef | 2.0 cd |
| 'Z88-8' | 6.3 abc | 5.7 a | 5.7 a | 4.3 a |
| 'Z88-14' | 6.7 ab | 5.3 a | 5.0 ab | 4.3 a |
| Avg. soil temp. (°F.) | 52 | 49 | 50 | 49 |

| | OBSERVATION DATE | | | |
|---|---|---|---|---|
| GRASS | 1-13-93 | 1-20-93 | 1-25-93 | 2-5-93 |
| 'El Toro' | 1.0 d | 2.0 ef | 2.3 de | 2.7 gh |
| 'Z88-8' | 4.3 a | 5.7 a | 7.0 a | 7.0 a |
| 'Z88-14' | 4.3 a | 5.3 a | 6.7 ab | 6.0 bc |
| Avg. soil temp. (°F.) | 52 | 53 | 53 | 55 |

| | OBSERVATION DATE | | | |
|---|---|---|---|---|
| GRASS | 2-12-93 | 2-17-93 | 2-24-93 | 3-3-93 |
| 'El Toro' | 5.0 de | 4.7 cd | 5.0 ef | 6.0 cdef |
| 'Z88-8' | 7.0 a | 7.0 a | 7.3 ab | 7.7 a |
| 'Z88-14' | 6.3 abc | 6.7 ab | 7.3 ab | 7.0 abc |
| Avg. soil temp. (°F.) | 56 | 56 | 55 | 55 |

Establishment Rate

Regarding establishment rate, it was found that 'El Toro' was the fastest to cover the soil surface with 70% coverage recorded five months following establishment and 100% coverage 10 months following establishment. In comparison, 'De Anza', referred to as Z88-8, provided about 57% coverage after 10 months and 'Victoria', referred to as Z88-14, provided about 34% coverage in the same time perid. 'De Anza' gave 92% coverage after 10 months and complete coverage 12 months following establishment; 'Victoria' gave nearly 60% coverage after 10 months and provided 100% coverage after 13 months. In comparison to other commercially available cultivars, 'De Anza' is quicker to establish than 'Emerald', 'Belair' and 'Meyer'; 'Victoria' was equal in establishment rate to 'Emerald' but faster than 'Belair' and 'Meyer'.

Consistently, winter color retention is greatest for 'De Anza' and 'Victoria' zoysiagrass. As an exmaple, in mid-January during the winter of 1991–1992, on a rating scale of 1–9 with 9 representing deep green color and 1 representing dormant, tan or light-brown color, 'De Anza' scored a 5.6, 'Victoria' a 6.0 and 'El Toro' a 2.2. Of the other commercially available cultivars, 'Emerald' scored 2.2, and 'Belair' and 'Meyer' scored a 1.0.

Other Comparisons

Leaf texture was observed in Summer, 1990 by measuring the leaf blade widths at the collar in mm. 'De Anza' and 'Victoria' were characterized as having an intermediate blade width (on a scale of coarse, intermediate and fine) with blade widths being about 2.72 and about 2.79 mm respectively. 'El Toro' was coarse with an average width of 3.41 mm/ 'Emerald' was fine textures with a width of 2.25 mm; 'Meyer' and 'Belair' both coarse textured with widths of 3.29 and 4.23 mm respectively.

The amount of seedhead expression was documented throughout the summer of 1990. 'De Anza', 'Victoria' and 'El Toro' produced more seedheads than did the commercially available cultivars 'Emerald', 'Belair' and 'Meyer'. Utilizing a low, medium and high rating system that was based on number of seedheads per square meter, 'De Anza', 'Victoria' and 'El Toro' were rated high and 'Emerald', 'Belair' and 'Meyer' were rated low.

All recording of turfgrass quality was also summarized in a low, medium and high category by cultivar. 'Victoria' was in the high category as was 'Emerald'; 'De Anza' and 'El Toro' were medium in overall quality ranking; and 'Meyer' and 'Belair' were in the low rank.

Similarly, 'Victoria' had the highest ranking for uniformity of turfgrass sward; 'De Anza', 'El Toro' and 'Emerald' were of medium ranking; and 'Belair' and 'Meyer' were rated low.

Leaf blade stiffness was on a 1 to 3 rating system with 1 representing a stiff blade and 3 representing a softer, less stiff blade, 'Victoria' was characterized as having a soft leaf blade; 'El Toro', 'Meyer' and 'Emerald' were rated intermediate with a score of 2; and 'De Anza' and 'Belair' were noted to have a stiff blade that characterized the cultivar.

Sod Density and Thatch Accumulation

Sod density was determined in July, 1994 at the University of California, Riverside Turfgrass Research Facility and at the University of California South Coast Research and Extension Center with density being defined as the number of tillers per unit area and reported on a low to high density scale. 'De Anza', 'Victoria', 'El Toro' and 'Meyer' were characterized as being of moderate density; 'Belair' was low density; and 'Emerald' was a high density cultivar. Thatch depth measurements taken at the University of California Turfgrass Research Facility in July, 1994, documented, in mm of thatch depth, that 'Emerald' produced the greatest depth of thatch (25.0 mm); 'Meyer', 'Belair' and 'Victoria' produced an intermediate thatch depth (b 18.0, 15.0 and 14.0 mm respectively); and 'El Toro' and 'De Anza' produced the lowest amount of thatch (11.67 and 10.33 mm respectively).

'De Anza' Botanical Description

The grass is a low-growing, perennial, attractive turfgrass that forms a moderately dense sward and spreads by tillers, rhizomes and stolons. The color is near 143 A.

The flat leaf blades range from about 1.8 to about 7.2 cm in length with an average of about 4.4 cm. Leaf widths range from about 1.9 to about 3.3 mm with an average of about 2.6 mm. Shorter leaves are lanceolate in shape while longer leaves become linear. Leaves are rolled in the bud. The ligule is ciliate with hairs about 1.4 to about 1.8 mm long at ligule area and with shorter hairs, averaging about 1.0 mm on both sides of ligule. Auricles are absent.

Stolon color is near 71 B. Stolon internode length ranges from about 1.6 to about 4.5 cm and averages about 2.7 cm. Stem thickness of the internodes ranges from about 1.1 to about 1.5 mm with an average of about 1.3 mm.

The inflorescence is a spikelike raceme ranging from about 1.3 to about 2.3 cm in length with an average of about 1.8 cm. Culm height averages 12 cm. Spikelets are one-flowered, appressed against a rachis and on a pedicel that averages about 1.6 mm long. A spikelet with anthers and stigma exerted range in color near 84 B to near 150 B, with the violet coloration often peripheral to the glume mid-rib. Mature spikelets are near 23 D and near 85 C near tip of glume.

It is evident from the foregoing that the new variety retains green coloration for a longer period of time than 'El Toro' and is, therefore, more desirable as a turf grass in geographical areas favoring its use.

It is claimed:

1. A new and distinct variety of Zoysiagrass named 'De Anza', substantially as described and illustrated, which has a longer growing season and green color retention in winter and less purple pigmentation than the variety 'El Toro'.

* * * * *

UNITED STATES PATENT AND TRADEMARK OFFICE

CERTIFICATE OF CORRECTION

PATENT NO. : Plant 9,127

DATED : May 2, 1995

INVENTOR(S) : Victor A. Gibeault; Matthew K. Leonard; Victor B. Youngner

It is certified that error appears in the above-indentified patent and that said Letters Patent is hereby corrected as shown below:

On the Title Page, after "[58] Field of Search" insert:

-- [56] References Cited

U.S. PATENT DOCUMENTS

| | | |
|---|---|---|
| P.P. 5,845 | 12/1986 | Younger...Plt./90 |
| P.P. 6,345 | 10/1988 | Whiting...Plt./90 |
| P.P. 6,516 | 1/1989 | Whiting...Plt./90 |
| P.P. 6,529 | 1/1989 | Pursley...Plt./90 |
| P.P. 7,074 | 12/1989 | Whiting...Plt./90 |
| P.P. 8,553 | 1/1994 | Staton....Plt./90 -- |

Column 1, line 24, before "tolerance" insert -- heat --.

Column 2, line 33, change "Jan. 3, 1994" to -- Jan. 13, 1994 --.

Column 5, line 6, change "perid" to -- period --.

Column 5, line 16, change "exmaple" to -- example --.

Column 5, line 32, change "3.41 mm/" to -- 3.41 mm; --.

Column 6, line 16, change "b 18.0" to -- 18.0 --.

Signed and Sealed this

Twenty-eighth Day of November 1995

*Attest:*

Bruce Lehman

BRUCE LEHMAN

*Attesting Officer*

*Commissioner of Patents and Trademarks*